(12) United States Patent
Kalpin

(10) Patent No.: US 8,162,888 B2
(45) Date of Patent: Apr. 24, 2012

(54) AUTOMATED CATHETER LENGTH DETERMINATION FOR IMPLANTABLE FLUID DELIVERY DEVICE

(75) Inventor: Scott L. Kalpin, Harris, MN (US)

(73) Assignee: Medtronic, Inc., Minneapolis, MN (US)

( * ) Notice: Subject to any disclaimer, the term of this patent is extended or adjusted under 35 U.S.C. 154(b) by 99 days.

(21) Appl. No.: 12/433,836

(22) Filed: Apr. 30, 2009

(65) Prior Publication Data

US 2010/0280446 A1 Nov. 4, 2010

(51) Int. Cl.
*A61M 31/00* (2006.01)
*A61M 1/00* (2006.01)
(52) U.S. Cl. .......................... 604/151; 604/67
(58) Field of Classification Search .................. 604/151, 604/131, 65–67, 891.1–892.1
See application file for complete search history.

(56) References Cited

U.S. PATENT DOCUMENTS

| | | | |
|---|---|---|---|
| 5,287,861 A * | 2/1994 | Wilk | 128/898 |
| 5,535,752 A | 7/1996 | Halperin et al. | |
| 7,320,676 B2 | 1/2008 | Miesel | |
| 2004/0125963 A1 | 7/2004 | Willis | |
| 2005/0288603 A1 | 12/2005 | Goping | |
| 2007/0270782 A1 | 11/2007 | Miesel et al. | |
| 2008/0228167 A1 | 9/2008 | Mittermeyer et al. | |

FOREIGN PATENT DOCUMENTS

| | | |
|---|---|---|
| EP | 1480008 A1 | 11/2004 |
| JP | 7113556 | 5/1995 |
| WO | 2007123764 A2 | 11/2007 |

OTHER PUBLICATIONS

Notification of Transmittal of the International Search Report and the Written Opinion for corresponding patent application No. PCT/US2010/022968, mailed May 7, 2010, 15 pages.

* cited by examiner

*Primary Examiner* — Nicholas Lucchesi
*Assistant Examiner* — Rebecca E Eisenberg
(74) *Attorney, Agent, or Firm* — Shumaker & Sieffert, P.A.

(57) ABSTRACT

Examples disclosed herein include methods and systems for automatically estimating the length of an implantable catheter by measuring the pressure decay response to pumping fluid through the catheter. The decay time for a unit fluid pressure pulse generated within the catheter is proportional to the length of the catheter, i.e. as the length of the catheter increases so does the decay time. The catheter length can therefore be estimated based on, e.g., the decay time of the pressure pulse. The estimated catheter length can also be analyzed to determine if it is representative of the actual length of the catheter, or, e.g., is affected by one or more catheter malfunctions including cuts and occlusions. Systems for automatically estimating catheter length include an implantable catheter, a pumping mechanism, a pressure sensor placed in a location to measure pressure within the catheter, and a processor that calculates the length of the catheter from a pressure pulse measured while fluid is delivered through the catheter.

22 Claims, 10 Drawing Sheets

AUTOMATED CATHETER LENGTH DETERMINATION FOR IMPLANTABLE FLUID DELIVERY DEVICE

TECHNICAL FIELD

The disclosure relates generally to implantable medical devices and, more particularly, to implantable fluid delivery systems.

BACKGROUND

A variety of medical devices are used for chronic, i.e., long-term, delivery of fluid therapy to patients suffering from a variety of conditions, such as chronic pain, tremor, Parkinson's disease, epilepsy, urinary or fecal incontinence, sexual dysfunction, obesity, spasticity, or gastroparesis. For example, pumps or other fluid delivery devices can be used for chronic delivery of therapeutic agents, such as drugs to patients. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device that can deliver a fluid medication to a patient at a selected site. A drug infusion device may be implanted at a location in the body of a patient and deliver a fluid medication through a catheter to a selected delivery site in the body. Drug infusion devices, such as implantable drug pumps, commonly include a reservoir for holding a supply of the therapeutic substance, such as a drug, for delivery to a site in the patient. The fluid reservoir can be self-sealing and accessible through one or more ports. A pump is fluidly coupled to the reservoir for delivering the therapeutic substance to the patient. A catheter provides a pathway for delivering the therapeutic substance from the pump to the delivery site in the patient.

Implantable drug delivery or infusion devices are commonly used, for example, when chronic administration of a pharmaceutically active agent or therapeutic substance to a patient is required. An implantable infusion pump-catheter delivery system may be preferred when it is important to deliver the agent to a specific site or when the agent must be administered on a recurrent basis in small, controlled dosages. Precise delivery of appropriate amounts of a fluid agent require accurate characterization of various delivery components of the system, such as the reservoir and catheter. The volume of the catheter, which is proportional to its length, is needed by the clinician or programmer, e.g., when determining the amount of drug needed to prime the entire pump and catheter. Catheter volume is also important when determining the time duration used to maintain a current infusion rate (bridging period) after refilling the pump's reservoir with a different fluid agent or fluid agent concentration to insure that the new infusion rate does not go into effect until the current drug has exited the catheter. Ordinarily, clinicians measure and record the length of catheter during implantation which is then used in calculation priming and bridging durations. However, there are a variety of ways for which this information fails to be recorded or is some how lost leaving clinicians that must manage patient's drug delivery therapies without the catheter length information vital to insuring that the prime and bridge procedures are safe.

SUMMARY

In general, this disclosure describes techniques for automatically estimating the length of a catheter of an implanted medical device. The techniques may measure a pressure decay response to pumping fluid doses through the catheter. The decay time for a unit fluid pressure pulse is proportional to the length of the catheter. In particular, as the length of the catheter increases, so does the pressure decay time. The catheter length can therefore be estimated based on the decay time of the pressure pulse.

In one example, a method includes delivering an amount of fluid through an implantable catheter. A pressure within a lumen of the catheter is measured during the delivery of the fluid to the patient. An estimated length for the catheter is calculated based on the measured pressure.

In another example, an implantable fluid delivery system includes a fluid delivery pump, a catheter, a pressure sensor, and a processor. The catheter is connected to the fluid delivery pump. The pressure sensor is arranged to measure a pressure in a lumen of the catheter. The processor is configured to control the fluid delivery pump to deliver an amount of fluid through the catheter, control the pressure sensor to measure a pressure within a lumen of the catheter during the delivery of the fluid through the catheter, and calculate an estimated length of the catheter based on the measured pressure.

In another example, a computer-readable medium contains instructions for causing a programmable processor to control a fluid delivery pump to deliver an amount of fluid through an implantable catheter, control a pressure sensor to measure a pressure within a lumen of the catheter during the delivery of the fluid through the catheter, and calculate an estimated length of the catheter based on the measured pressure.

In still another example, a device includes means for delivering an amount of fluid through an implantable catheter, means for measuring a pressure within a lumen of the catheter during the delivery of the fluid through the catheter, and means for calculating an estimated length of the catheter based on the measured pressure.

The details of one or more examples disclosed herein are set forth in the accompanying drawings and the description below. Other features, objects, and advantages will be apparent from the description and drawings, and from the claims.

DETAILED DESCRIPTION

Figure 1:
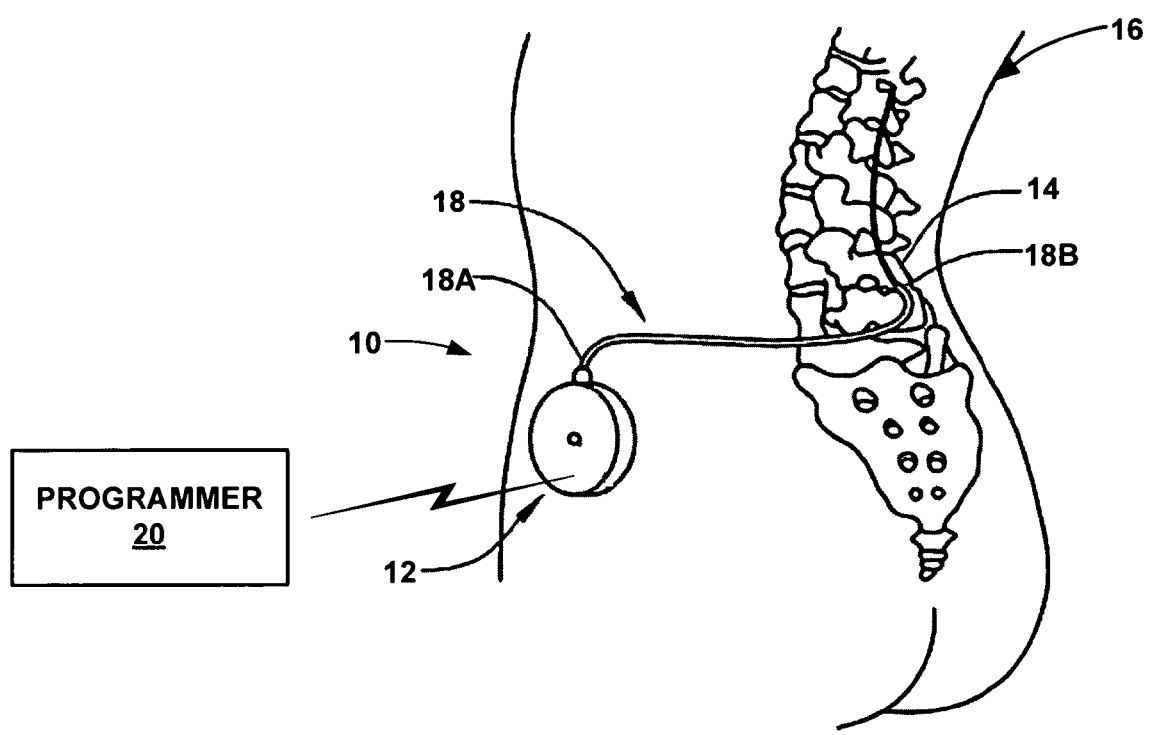
FIG. 1 is a conceptual diagram illustrating an example of a fluid delivery system including an implantable fluid delivery device configured to deliver a fluid therapeutic agent to a patient via a catheter.

Medical devices are useful for treating, managing or otherwise controlling various patient conditions or disorders including, e.g., pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, or other disorders. Some medical devices, referred to herein generally as fluid delivery devices may be configured to deliver one or more fluid therapeutic agents, alone or in combination with other therapies, such as electrical stimulation, to one or more target sites within a patient. For example, in some cases, a fluid delivery device may deliver pain-relieving drug(s) to patients with chronic pain, insulin to a patient with diabetes, or other fluids to patients with different disorders. The device may be implanted in the patient for chronic therapy delivery (i.e., longer than a temporary, trial basis) or temporary delivery.

As used in this disclosure, the terms dosing program or therapy program generally refer to a program sent to an implantable fluid delivery device by a programming device to cause the fluid delivery device to deliver fluid at a certain rate and at a certain time. The dosing program may include, for example, definitions of a priming bolus, a bridging bolus, a supplemental bolus, and a therapy schedule. A dosing program may include additional information, such as patient information, permissions for a user to add a supplemental bolus, as well as limits on the frequency or number of such boluses, historical therapy schedules, fluid or drug information, or other information.

The term therapy schedule may generally refer to a rate (which may be zero) at which to administer a fluid, or a drug or drug combination within the fluid, at specific times to a patient. In particular, the therapy schedule may define one or more programmed doses, which may be periodic or aperiodic, each dose including, e.g., a rate of fluid delivery and a time duration for which to deliver the dose. Dose generally refers to the amount of drug delivered over a period of time, and may change over the course of a therapy schedule such that a drug may be delivered at different rates at different times.

A priming bolus refers to a bolus delivered by the implantable fluid delivery device to move the fluid to the distal tip of the catheter, e.g., the tip of the catheter that is remote from the reservoir and internal tubing. Once the fluid is primed to the distal tip of the catheter, the device is ready to deliver fluid to the patient from the distal tip, e.g., via one or more fluid outlets at or near the distal tip. The device delivers the priming bolus during a priming phase to prepare the device for delivery of the fluid to the patient.

In addition to a priming bolus, an implantable fluid delivery device may also perform a bridging bolus, which can also be referred to as a bridge. Bridges are performed when a new fluid is inserted into a reservoir of the device while an old fluid is still present in the device, e.g., within internal tubing of the device and/or within a catheter connected to the device. The bridge is performed to define a rate at which to deliver the old fluid until the old fluid is completely delivered out of the catheter and to the patient such that the device contains only the new fluid.

In general, there may be only one priming bolus per implanted device, because only at or around implantation of the device in the patient is the fluid pathway between the device and the target delivery site partially or completely free from any fluid such that priming is necessary. Boluses after the priming bolus that prepare the device to deliver a therapeutic agent to the patient, i.e. fill the fluid pathway from the device to the target delivery site with the agent, may be referred to as bridging boluses.

A supplemental bolus is a bolus administered to the patient outside of the therapy schedule. The terms independent bolus, one-time bolus, and therapeutic bolus may also be used in this disclosure to refer to a supplemental bolus. In one example, the implantable fluid delivery device may administer a supplemental bolus before the implantable fluid delivery device begins administering doses of fluid according to the therapy schedule. In another example, the implantable fluid delivery device may administer a supplemental bolus during the therapy schedule, e.g., to override or supplement the therapy schedule in response to clinician instruction or patient request.

One task required with implantable infusion therapy systems is calculating priming and/or bridging boluses. Miscalculations of priming or bridging bolus amount can result in undesirable overdose or underdose scenarios. A parameter used to calculate the duration of a bridge or priming bolus is the volume of the catheter, which is directly proportional to the implanted catheter length. The catheter length may vary according to the distance between the implantable pump and a target delivery site within the patient.

It is typically the responsibility of the implanting physician to manually measure and record the catheter length. In many cases, implantable catheters come in standard lengths and are cut to fit a particular implantation. In such cases, the physician may measure the length cut off from the catheter at implantation and calculate the length of the implanted catheter by subtracting the cut off length from the full length of the catheter prior to being cut. In any event, if this recording is done in error or not at all, then the subsequent bolus calculations will also be subject to error, which in turn can lead to conditions including overdosing or underdosing the patient in which the device is implanted. In some instances, the catheter and/or fluid delivery device may need to be explanted or surgically exposed to measure the length of the catheter.

It may be difficult to deliver appropriate priming and/or bridging boluses when the recorded catheter length is not accurate. Techniques described in this disclosure may incorporate the use of therapy systems with one or more pressure sensors configured to measure pressure somewhere within the fluid pathway of an implantable fluid delivery device, such as a catheter extending from the device and/or internal tubing within the device. Such techniques may be performed when the catheter is implanted or outside the body prior to implantation. In some cases, pressure may be measured while a dose of the therapeutic agent is delivered to the patient.

The fluid delivery device in such therapy systems, and/or another device such as an external programmer, may be configured to automatically calculate an estimated length of the catheter based on the measured pressure. Automatic calculation of the length of the catheter without relying on human intervention, e.g., without requiring the implanting physician to measure and record length, can promote accurate catheter length recording. Hence, in some cases, cathether length may be estimated automatically instead of by the clinician. Accurate catheter length recording may promote proper delivery of priming and bridging boluses, or other doses in which accurate determination of catheter length is important to proper and safe delivery of the therapeutic agent to the patient.

FIG. 1 is a conceptual diagram illustrating an example of a therapy system 10, which includes implantable medical device (IMD) 12, catheter 18, and external programmer 20. IMD 12 is connected to catheter 18 to deliver at least one therapeutic agent, such as a pharmaceutical agent, pain relieving agent, anti-inflammatory agent, gene therapy agent, or the like, to a target site within patient 16. Example therapeutic agents that IMD 12 can be configured to deliver include, but are not limited to, insulin, morphine, hydromorphone, bupivacaine, clonidine, other analgesics, genetic agents, antibiotics, nutritional fluids, hormones or hormonal drugs, gene therapy drugs, anticoagulants, cardiovascular medications or chemotherapeutics.

In the example of FIG. 1, the therapeutic agent is a therapeutic fluid, which IMD 12 delivers to patient 16 through catheter 18 from proximal end 18A coupled to IMD 12 to distal end 18B located proximate to the target site. Catheter 18 can comprise a unitary catheter or a plurality of catheter segments connected together to form an overall catheter length. External programmer 20 is configured to wirelessly communicate with IMD 12 as needed, such as to provide or retrieve therapy information or control aspects of therapy delivery (e.g., modify the therapy parameters such as rate or timing of delivery, turn IMD 12 on or off, and so forth) from IMD 12 to patient 16.

IMD 12, in general, may have an outer housing that is constructed of a biocompatible material that resists corrosion and degradation from bodily fluids including, e.g., titanium or biologically inert polymers. IMD 12 may be implanted within a subcutaneous pocket relatively close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic agent. In still other examples, IMD 12 may be external to patient 16 with a percutaneous catheter connected between IMD 12 and the target delivery site within patient 16.

Catheter 18 may be coupled to IMD 12 either directly or with the aid of a catheter extension (not shown in FIG. 1). In the example shown in FIG. 1, catheter 18 traverses from the implant site of IMD 12 to one or more targets proximate to spine 14. Catheter 18 is positioned such that one or more fluid delivery outlets (not shown in FIG. 1) of catheter 18 are proximate to the one or more targets within patient 16. In the example of FIG. 1, IMD 12 delivers a therapeutic agent through catheter 18 to one or more targets proximate to spinal cord 14. IMD 12 can be configured for intrathecal drug delivery into the intrathecal space or epidural delivery into the epidural space, both of which surround spinal cord 14. The epidural space (also known as "extradural space" or "peridural space") is the space within the spinal canal (formed by the surrounding vertebrae) lying outside the dura mater, which encloses the arachnoid mater, subarachnoid space, the cerebrospinal fluid, and spinal cord 14. The intrathecal space is within the subarachnoid space, which is past the epidural space and dura mater and through the theca.

Although the target site shown in FIG. 1 is proximate to spinal cord 14 of patient 16, other applications of therapy system 10 include alternative target delivery sites. The target delivery site in other applications of therapy system 10 can be located within patient 16 proximate to, e.g., sacral nerves (e.g., the S2, S3, or S4 sacral nerves) or any other suitable nerve, organ, muscle or muscle group in patient 16, which may be selected based on, for example, a patient condition. In one such application, therapy system 10 may be used to deliver a therapeutic agent to tissue proximate to a pudendal nerve, a perineal nerve or other areas of the nervous system, in which cases, catheter 18 would be implanted and substantially fixed proximate to the respective nerve. Positioning catheter 18 to deliver a therapeutic agent to various sites within patient 16 enables therapy system 10 to assist in managing, e.g., peripheral neuropathy or post-operative pain mitigation, ilioinguinal nerve therapy, intercostal nerve therapy, gastric stimulation for the treatment of gastric motility disorders and/or obesity, and muscle stimulation, or for mitigation of other peripheral and localized pain (e.g., leg pain or back pain). As another example delivery site, catheter 18 may be positioned to deliver a therapeutic agent to a deep brain site or within the heart (e.g., intraventricular delivery of the agent). Delivery of a therapeutic agent within the brain may help manage any number of disorders or diseases including, e.g., depression or other mood disorders, dementia, obsessive-compulsive disorder, migraines, obesity, and movement disorders, such as Parkinson's disease, spasticity, and epilepsy. Catheter 18 may also be positioned to deliver insulin to a patient with diabetes.

As already mentioned, therapy system 10 can be used to reduce pain experienced by patient 16. In such an application, IMD 12 can deliver one or more therapeutic agents to patient 16 according to one or more dosing programs that set forth different therapy parameters, such as a therapy schedule specifying programmed doses, dose rates for the programmed doses, and specific times to deliver the programmed doses. The dosing programs may be a part of a program group for therapy, where the group includes a plurality of dosing programs and/or therapy schedules. In some examples, IMD 12 may be configured to deliver a therapeutic agent to patient 16 according to different therapy schedules on a selective basis. IMD 12 may include a memory to store one or more therapy programs, instructions defining the extent to which patient 16 may adjust therapy parameters, switch between dosing programs, or undertake other therapy adjustments. Patient 16 or a clinician may select and/or generate additional dosing programs for use by IMD 12 via external programmer 20 at any time during therapy or as designated by the clinician.

In some examples, multiple catheters 18 may be coupled to IMD 12 to target the same or different tissue or nerve sites within patient 16. Thus, although a single catheter 18 is shown in FIG. 1, in other examples, system 10 may include multiple catheters or catheter 18 may define multiple lumens for delivering different therapeutic agents to patient 16 or for delivering a therapeutic agent to different tissue sites within patient 16. Accordingly, in some examples, IMD 12 may include a plurality of reservoirs for storing more than one type of therapeutic agent. In some examples, IMD 12 may include a single long tube that contains the therapeutic agent in place of a reservoir. However, for ease of description, an IMD 12 including a single reservoir is primarily discussed herein with reference to the example of FIG. 1.

Programmer 20 is an external computing device that is configured to communicate with IMD 12 by wireless telemetry. For example, programmer 20 may be a clinician programmer that the clinician uses to communicate with IMD 12. Alternatively, programmer 20 may be a patient programmer that allows patient 16 to view and modify therapy parameters. The clinician programmer may include additional or alternative programming features than the patient programmer. For example, more complex or sensitive tasks may only be allowed by the clinician programmer to prevent patient 16 from making undesired or unsafe changes to the operation of IMD 12.

Programmer 20 may be a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate though the user interface of programmer 20 and provide input.

If programmer 20 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 20 may be a touch screen that allows the user to provide input directly to the user interface shown on the display. The user may use a stylus or their finger to provide input to the display.

In other examples, rather than being a handheld computing device or a dedicated computing device, programmer 20 may be a larger workstation or a separate application within another multi-function device. For example, the multi-function device may be a cellular phone, personal computer, laptop, workstation computer, or personal digital assistant that can be configured with an application to simulate programmer 20. Alternatively, a notebook computer, tablet computer, or other personal computer may enter an application to become programmer 20 with a wireless adapter connected to the personal computer for communicating with IMD 12.

When programmer 20 is configured for use by the clinician, programmer 20 may be used to transmit initial programming information to IMD 12. This initial information may include hardware information for system 10 such as the type of catheter 18, the position of catheter 18 within patient 16, the length of catheter 18 at implantation as measured by the implanting physician and/or as automatically estimated by IMD 12, the type of therapeutic agent(s) delivered by IMD 12, a baseline orientation of at least a portion of IMD 12 relative to a reference point, therapy parameters of therapy programs stored within IMD 12 or within programmer 20, and any other information the clinician desires to program into IMD 12.

The clinician uses programmer 20 to program IMD 12 with one or more therapy programs that define the therapy delivered by the IMD. During a programming session, the clinician may determine one or more dosing programs that may provide effective therapy to patient 16. Patient 16 may provide feedback to the clinician as to efficacy of a program being evaluated or desired modifications to the program. Once the clinician has identified one or more programs that may be beneficial to patient 16, the patient may continue the evaluation process and determine which dosing program or therapy schedule best alleviates the condition of the patient or otherwise provides efficacious therapy to the patient.

The dosing program information may set forth therapy parameters, such as different predetermined dosages of the therapeutic agent (e.g., a dose amount), the rate of delivery of the therapeutic agent (e.g., rate of delivery of the fluid), the maximum acceptable dose, a time interval between successive supplemental boluses such as patient-initiated boluses (e.g., a lock-out interval), a maximum dose that may be delivered over a given time interval, and so forth. IMD 12 may include a feature that prevents dosing the therapeutic agent in a manner inconsistent with the dosing program. Programmer 20 may assist the clinician in the creation/identification of dosing programs by providing a methodical system of identifying potentially beneficial therapy parameters.

A dosage of a therapeutic agent, such as a drug, may be expressed as an amount of drug, e.g., measured in milligrams or other volumetric units, provided to patient 16 over a time interval, e.g., per day or twenty-four hour period. In this sense, the dosage may indicate a rate of delivery. This dosage amount may convey to the caregiver an indication of the probable efficacy of the drug and the possibility of side effects. In general, a sufficient amount of the drug should be administered in order to have a desired therapeutic effect, such as pain relief. However, the amount of the drug administered to the patient should be limited to a maximum amount, such as a maximum daily dose, in order not to avoid potential side effects. Program information specified by a user via programmer 20 may be used to control dosage amount, dosage rate, dosage time, maximum dose for a given time interval (e.g., daily), or other parameters associated with delivery of a drug or other fluid by IMD 12.

In some cases, programmer 20 may also be configured for use by patient 16. When configured as the patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 need to be replaced or recharged.

Whether programmer 20 is configured for clinician or patient use, programmer 20 may communicate to IMD 12 or any other computing device via wireless communication. Programmer 20, for example, may communicate via wireless communication with IMD 12 using radio frequency (RF) telemetry techniques. Programmer 20 may also communicate with another programmer or computing device via a wired or wireless connection using any of a variety of communication techniques including, e.g., RF communication according to the 802.11 or Bluetooth specification sets, infrared (IR) communication according to the IRDA specification set, or other standard or proprietary telemetry protocols. Programmer 20 may also communicate with another programming or computing device via exchange of removable media, such as magnetic or optical disks, or memory cards or sticks including, e.g., non-volatile memory. Further, programmer 20 may communicate with IMD 12 and another programmer via, e.g., a local area network (LAN), wide area network (WAN), public switched telephone network (PSTN), or cellular telephone network, or any other terrestrial or satellite network appropriate for use with programmer 20 and IMD 12.

In accordance with catheter length determination techniques described in detail below with reference to FIGS. 3-8, therapy system 10 of FIG. 1 may include one or more pressure sensors that are configured to measure a pressure pulse within catheter 18 during the delivery of a fluid dose. The fluid dose may be an actual fluid dose delivered within patient 16, a test dose delivered outside the patient, or a test dose of a test fluid delivered within the patient. IMD 12 includes control electronics, e.g. one or more processors and non-volatile memories that are configured to receive the measured pressure pulse within catheter 18 from the pressure sensor(s) and calculate an estimated length of catheter 18 based on the pressure pulse.

Measuring the pressure pulse within catheter 18 can include determining a maximum pressure within the catheter and determining a decay time of the pressure pulse. The decay time of a pressure pulse, generally speaking, is the time required for the pressure pulse within the catheter to fall from a first pressure level to a second pressure level. The first pressure level may be a maximum pressure level sensed upon delivery of a fluid amount and the second pressure level may be a baseline pressure. The baseline pressure level may be a pressure sensed before of after the delivery of the fluid amount. IMD 12 can be configured to measure a baseline pressure within the catheter while no fluid dose is being delivered to the patient. In some examples, the baseline pressure can be measured prior to delivering the fluid dose to the patient through the catheter.

Calculating the estimated length of the catheter can include, e.g., calculating the estimated length of the catheter based on the decay time. The estimated length may be calculated automatically, e.g., by IMD 12 or programmer 20, avoiding the need for human intervention. In some cases, the estimated length may be calculated automatically and manually by a human caregiver, such that the automated calculation may be used as a cross-verification check to ensure that the human-measured length is generally accurate. Pressure measurement to estimate catheter length may be performed when the catheter is implanted in the patient (in vivo) or when the catheter is outside the patient prior to implantation (ex vivo).

Additionally, IMD 12 can be configured to analyze the estimated length to determine if it is representative of an actual length of the catheter. In some cases, catheter 18 may become disconnected from IMD 12 or otherwise malfunction due to, e.g., cuts or occlusions in the catheter. IMD 12 can therefore discern whether the estimated length that is calculated based on the pressure pulse is representative of the actual length of catheter 18 by identifying conditions indicative of one or more catheter malfunctions. For example, IMD 12 can determine if the maximum pressure of the pressure pulse is below a minimum pressure threshold value, which may indicate the presence of an air bubble in the fluid pathway or that catheter 18 is disconnected completely from IMD 12. Additionally, IMD 12 can determine if the decay time is below a minimum threshold value, which may indicate a leak in catheter 18. In another example, IMD 12 can determine if the decay time is above a maximum threshold value, which may indicate an occlusion in catheter 18. IMD 12 can also analyze the pressure pulse by determining if the pressure within the lumen falls below a baseline pressure after decaying from a maximum pressure, which may indicate either a cut in catheter 18 or that catheter 18 is disconnected from IMD 12.

In general, the estimated length may be used to generate a catheter length value for presentation to a user, such as a clinician, e.g., via a user interface external programmer 20. The clinician then may select the estimated catheter length for use by programmer 20 and/or IMD 12 in calculating appropriate dosage parameters, including parameters for priming and/or bridging boluses. In some cases, the estimated catheter length produced based on the pressure measurements may be used as a cross-verification check to ensure that a previously determined catheter length, such as a catheter length determined by a clinician or other user, is reasonably accurate.

If the automatically estimated catheter length and the catheter length estimated by the clinician are inconsistent, programmer 20 and/or IMD 12 may be configured to use the automatically estimated catheter length to compute or recompute dosage parameters, or the programmer and/or IMD may present an alert to the clinician or other user indicating the inconsistency. In some cases, although the catheter length determination may be described as automatic, a user such as a clinician may control programmer 20 and/or IMD 12 to initiate the automated catheter length determination at a desired time.

Figure 2:
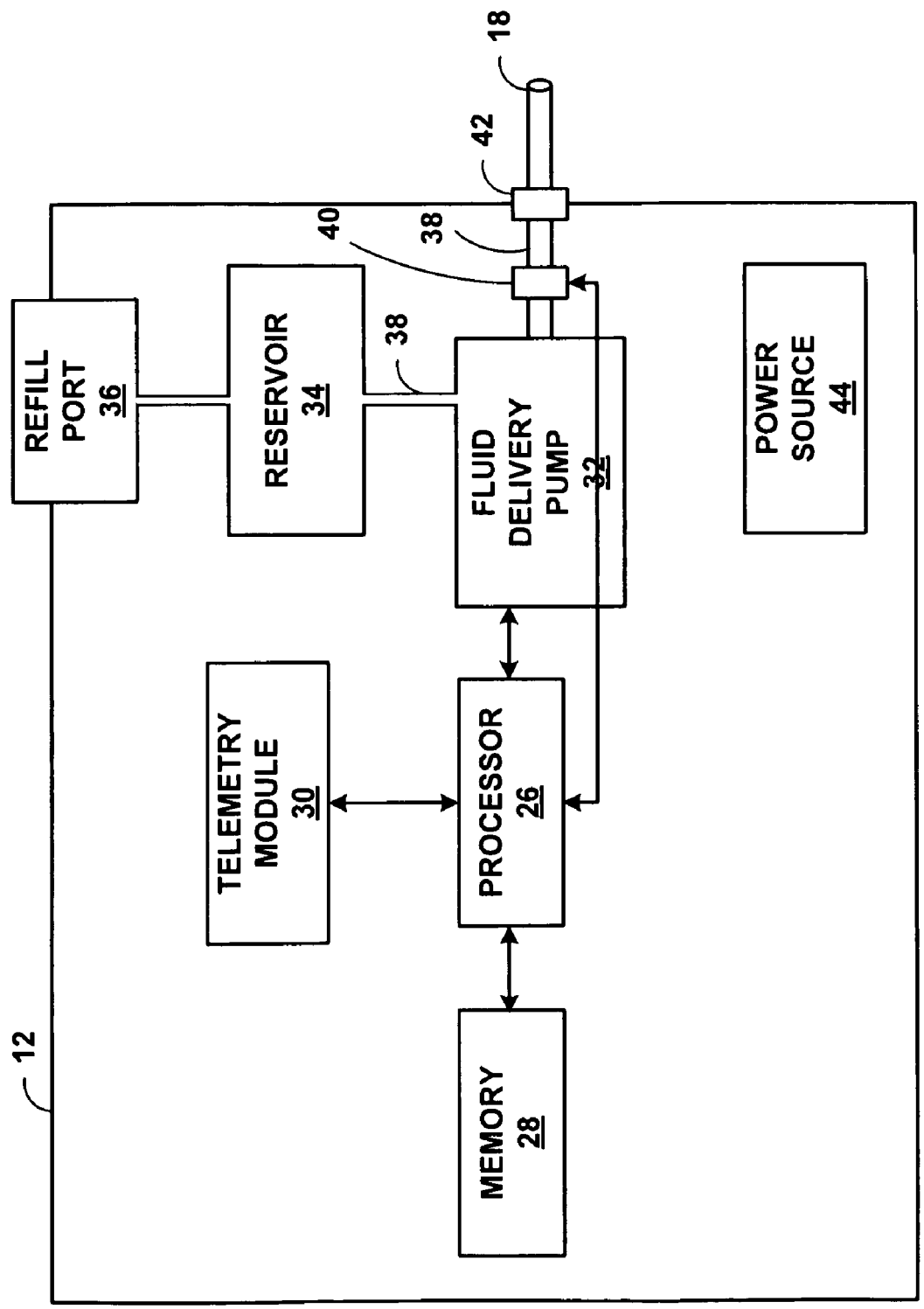
FIG. 2 is functional block diagram illustrating an example of the implantable fluid delivery device of FIG. 1.

FIG. 2 is a functional block diagram illustrating components of an example of IMD 12, which includes processor 26, memory 28, telemetry module 30, fluid delivery pump 32, reservoir 34, refill port 36, internal tubing 38, pressure sensor 40, catheter access port 42, and power source 44. Processor 26 is communicatively connected to memory 28, telemetry module 30, fluid delivery pump 32, and pressure sensor 40. Fluid delivery pump 32 is connected to reservoir 34 and internal tubing 38. Reservoir 34 is connected to refill port 36. Pressure sensor 40 is arranged in internal tubing 38 between pump 32 and catheter access port 42. Measurements obtained by pressure sensor 40 may be received by processor 26 and stored in memory 28 by the processor. Catheter access port 42 is connected to internal tubing 38 and catheter 18. IMD 12 also includes power source 44, which is configured to deliver operating power to various components of the IMD.

During operation of IMD 12, processor 26 controls fluid delivery pump 32 with the aid of instructions associated with program information that is stored in memory 28 to deliver a therapeutic agent to patient 16 via catheter 18. Instructions executed by processor 26 may, for example, define dosing programs that specify the amount of a therapeutic agent that is delivered to a target tissue site within patient 16 from reservoir 30 via catheter 18. The instructions may further specify the time at which the agent will be delivered and the time interval over which the agent will be delivered. The amount of the agent and the time over which the agent will be delivered are a function of, or alternatively determine, the dosage rate at which the fluid is delivered. The therapy programs may also include other therapy parameters, such as the frequency of bolus delivery, the type of therapeutic agent delivered if IMD 12 is configured to deliver more than one type of therapeutic agent, and so forth. Components described as processors within IMD 12, external programmer 20, or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Upon instruction from processor 26, fluid delivery pump 32 draws fluid from reservoir 34 and pumps the fluid through internal tubing 38 to catheter 18 through which the fluid is delivered to patient 16 to effect one or more of the treatments described above. Internal tubing 38 is a segment of tubing or a series of cavities within IMD 12 that run from reservoir 34, around or through fluid delivery pump 32 to catheter access port 42. Fluid delivery pump 32 can be any mechanism that delivers a therapeutic agent in some metered or other desired flow dosage to the therapy site within patient 16 from reservoir 30 via implanted catheter 18.

In one example, fluid delivery pump 32 can be a squeeze pump that squeezes internal tubing 38 in a controlled manner, e.g., such as a peristaltic pump, to progressively move fluid from reservoir 34 to the distal end of catheter 18 and then into patient 16 according to parameters specified by a set of program information stored on memory 28 and executed by processor 26. Fluid delivery pump 32 can also be an axial pump, a centrifugal pump, a pusher plate, a piston-driven pump, or other means for moving fluid through internal tubing 38 and catheter 18. In one particular example, fluid delivery pump 32 can be an electromechanical pump that delivers fluid by the application of pressure generated by a piston that moves in the presence of a varying magnetic field and that is configured to draw fluid from reservoir 34 and pump the fluid through internal tubing 38 and catheter 18 to patient 16.

Periodically, fluid may need to be supplied transcutaneously to reservoir 34 because all of a therapeutic agent has been or will be delivered to patient 16, or because a clinician wishes to replace an existing agent with a different agent or similar agent with different concentrations of therapeutic ingredients. Refill port 26 can therefore comprise a self-sealing membrane to prevent loss of therapeutic agent delivered to reservoir 30 via refill port 26. For example, after a percutaneous delivery system, e.g., a hypodermic needle, penetrates the membrane of refill port 26, the membrane may seal shut when the needle is removed from refill port 26.

Pump 32 may deliver fluid in controlled pulses. When pump 32 is called upon by processor 26 to deliver a fluid dose through catheter 18, processor 26 may also control pressure sensor 40 to measure a pressure pulse within catheter 18 that is generated by the delivery of fluid through catheter 18. Pressure sensor 40 can also measure a steady state baseline pressure within catheter 18 when no fluid dose is being delivered to patient 16. As will be discussed in greater detail below, pressure sensor 40 can be any of a number of types of sensors that are capable of measuring the pressure within an implantable catheter including, e.g. capacitive and inductive pressure sensors.

Pressure sensor 40 can read either gauge or absolute pressure of the fluid in catheter 18. Because methods disclosed herein rely on comparison of pressure just prior to and during delivery of a fluid dose to a patient through the catheter 18, changes in ambient pressure may be of reduced importance in implementing examples according to this disclosure (especially where the successive pulses are delivered within relatively short time frames, e.g., within minutes or even seconds of each other).

In those instances where, however, it is desirable to use pressure measurements from sensor 40 that are adjusted to account for ambient pressure outside of the catheter 18, a reference pressure may be detected within the body of patient 16 in which catheter 18 is implanted or may be detected outside of the patient's body. When detected within the body of patient 16, a reference pressure may be detected in a location near IMD 12 or the target delivery site near distal end 18B of catheter 18, or even in a location in a separate area of the patient's body. A reference pressure may be obtained in any location capable of providing a pressure indicative of the external environment of implanted catheter 18.

In one example, an infusion system may include a catheter 18 having a first lumen for delivering a fluid and a second lumen through which no fluid is delivered. A reference pressure may then be detected in the second lumen. The second lumen in catheter 18 can be used to obtain a reference pressure from distal end 18B of catheter 18, from a region near the target delivery site of therapy system 10. An expanded explanation of reference pressures may be found in commonly assigned U.S. Pat. No. 7,320,676, entitled PRESSURE SENSING IN IMPLANTABLE MEDICAL DEVICES, by Miesel.

The pressure pulse(s) measured by pressure sensor 40 during delivery of a fluid dose to patient 16 can be stored in memory 28. Processor 26 can access one or more stored pressure pulses to calculate an estimated length of catheter 18 based on an algorithm, group of algorithms, or a series of executable steps in any form, which may also be stored in memory 28. Processor 26 may also rely on one or more look-up tables, or other data aggregations stored in memory 28 to calculate the estimated length of catheter 18. For example, processor 26 may retrieve stored pressure pulses from a look-up table in memory 28. Processor 26 may also analyze the estimated length calculation to determine whether the estimate is representative of an actual length of catheter 18. Analyzing the estimated length can be executed using the same or a different algorithm used for calculating the estimated length, which may also be stored in memory 28 of IMD 12. Memory 28 may include any volatile or non-volatile media, such as a random access memory (RAM), read only memory (ROM), non-volatile RAM (NVRAM), electrically erasable programmable ROM (EEPROM), flash memory, and the like.

Although controlling fluid pump 32 and sensor 40 to deliver fluid through catheter 18 and measure a pressure pulse therein has been described as executed by IMD 12, and in particular, processor 26, in other examples one or more of these functions may be carried out by other devices including, e.g., external programmer 20. For example, a user may interact with external programmer 20 to command processor 26 of IMD 12 to control fluid pump 32 to deliver a fluid dose to patient 16 through catheter 18. Thereafter, pressure sensor 40 may measure a pressure pulse within catheter 18 during delivery of the fluid dose and processor 26 may control telemetry module 30 to transmit the measured pressure pulse data to external programmer 20. External programmer 20 may, in some cases, store the measured pressure pulse data in one or more non-volatile memories included in the programmer. In any event, a processor housed within programmer 20 may calculate an estimated length of catheter 18 based on the measured pressure pulse received from IMD 12 in accordance with the techniques described below with reference to FIGS. 3-8.

In addition to storing pressure pulse measurement data obtained by pressure sensor 40 and one or more algorithms used to execute example methods according to this disclosure, memory 28 may store program information including instructions for execution by processor 26, such as, but not limited to, therapy programs, historical therapy programs, timing programs for delivery of fluid from reservoir 34 to catheter 18, and any other information regarding therapy of patient 16. A program may indicate the bolus size or flow rate of the drug, and processor 26 may accordingly deliver therapy. A program may also indicate the frequency at which pressure sensor 40 is commanded to measure a pressure pulse and, as will be discussed in greater detail below, instructions for estimating the length of catheter 18 based on one or more measured pressure pulses. Memory 28 may include separate memories for storing instructions, patient information, therapy parameters (e.g., grouped into sets referred to as "dosing programs"), therapy adjustment information, program histories, and other categories of information such as any other data that may benefit from separate physical memory modules. Therapy adjustment information may include information relating to timing, frequency, rates and amounts of patient boluses or other permitted patient modifications to therapy. In some examples, memory 28 stores program instructions that, when executed by processor 26, cause IMD 12 and processor 26 to perform the functions attributed to them in this disclosure.

At various times during the operation of IMD 12 to treat patient 16, communication to and from IMD 12 may be necessary to, e.g., change therapy programs, adjust parameters within one or more programs, configure or adjust a particular bolus, send or receive an estimated length of catheter 18, or to otherwise download information to or from IMD 12. Processor 26 therefore controls telemetry module 30 to wirelessly communicate between IMD 12 and other devices including, e.g. programmer 20. Telemetry module 30 in IMD 12, as well as telemetry modules in other devices described herein, such as programmer 20, can be configured to use RF communication techniques to wirelessly send and receive information to and from other devices respectively. In addition, telemetry module 30 may communicate with programmer 20 via proximal inductive interaction between IMD 12 and the external programmer. Telemetry module 30 may send information to external programmer 20 on a continuous basis, at periodic intervals, or upon request from the programmer.

Power source 44 delivers operating power to various components of IMD 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As another alternative, an external inductive power supply could transcutaneously power IMD 12 as needed or desired.

Figure 3:
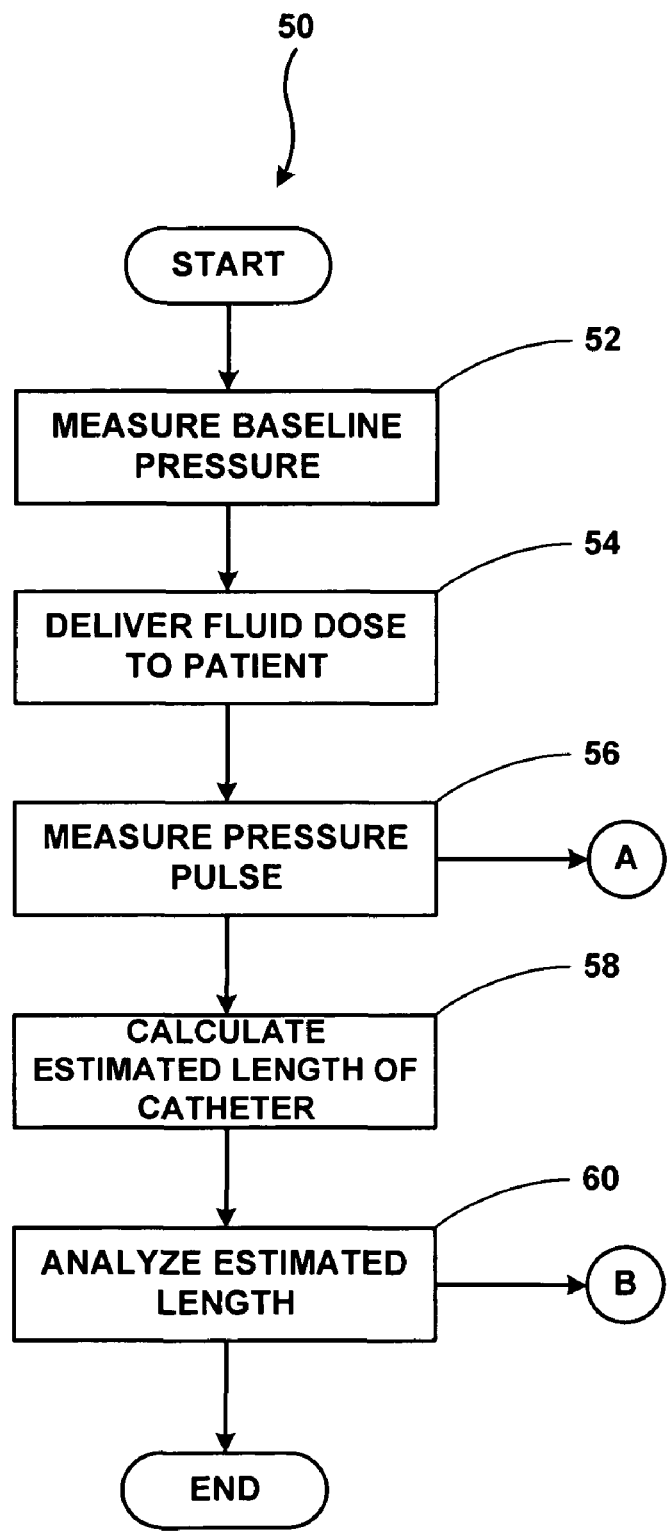
FIG. 3 is a flowchart illustrating a method of determining a length of an implantable catheter used with an implantable fluid delivery device.

FIG. 3 is a flow chart illustrating an example method of determining a length of an implantable catheter. Method 50 includes measuring a baseline pressure within a lumen of the catheter while no fluid dose is being delivered to the patient (step 52), delivering a fluid dose to a patient through the catheter (step 54), measuring a pressure pulse within the lumen of the catheter during the delivery of the fluid dose to the patient (step 56), calculating an estimated length of the catheter based on the measured pressure pulse (step 58), and analyzing the estimated length to determine if it is representative of an actual length of the catheter (step 60). Thereafter, or at any other time during the execution of methods according to this disclosure measured pressure pulse, estimated length, and data relating to the analysis of the estimated length may be stored temporarily or permanently stored in, e.g., a non-volatile memory.

Method 50, as well as other examples according to this disclosure can be implemented using, e.g. processor 26 of IMD 12 shown in FIGS. 1 and 2 to execute one or more algorithms stored in memory 28. In other examples, however, method 50 may be carried out using the control electronics, e.g. internal memory and processor of an external fluid delivery device that controls delivery of a therapeutic agent through a transcutaneous catheter. In still another example, method 50 may be carried out cooperatively by more than one device including, e.g., external programmer 20 and IMD 12, which receives pressure measurement data from IMD 12 by wireless telemetry. Method 50 is generally directed to automatically determining, i.e. without the need for human interaction, the length of an implantable catheter based on the characteristics of a pressure pulse generated within the catheter during delivery of a fluid dose to a patient. Determining the length of the implanted catheter without relying on the implanting physician measuring and recording length can assist in and improve proper delivery of, e.g., priming and bridging boluses, or any other doses in which catheter length is critical to proper and safe delivery of the therapeutic agent to the patient.

One task required with implantable infusion therapies is the calculation of priming and/or bridging boluses. Miscalculation of the bolus duration can result in undesirable overdose or underdose scenarios. A key parameter used to calculate the duration of a bridge or priming bolus is the volume of the catheter, which is directly proportional to the implanted catheter length. In particular, given a known catheter lumen diameter, the catheter length is used to calculate catheter volume. It is typically the responsibility of the implanting physician to manually measure and record the catheter length. However, if this recording is done in error or not at all, then the subsequent bolus calculations will also be subject to error, which in turn can lead to conditions including overdosing or underdosing the patient in which the device is implanted.

Examples disclosed herein therefore may augment or replace the need for manually entering the catheter length in implantable fluid delivery systems, reducing the possibility of miscalculating dosing durations including, e.g. the duration of a bridge or priming bolus. These example methods and systems can be important when a patient changes clinics or is out of the area in which his or her clinic is located and needs to have a pump refilled with a new drug, in which case the patient may need a bridging bolus. If the catheter type and length is not available, this method may allow a reasonable estimate of the dead space to be calculated for the switch over from one drug to another.

Referring again to FIG. 3, method 50 initially involves processor 26 controlling pressure sensor 40 to measure a baseline pressure within the lumen of catheter 18 while no fluid dose is being delivered to patient 16 (step 52). In order to establish a reference pressure within catheter 18, method 50 may include measuring the pressure within the lumen of the catheter while it is full of fluid but not during delivery of any fluid dose to the patient. Measuring the pressure under these conditions will establish the baseline pressure from which other conditions can be judged, e.g., the pressure pulse generated within the catheter during delivery of a fluid dose to the patient. The baseline pressure can be measured (step 52) by pressure sensor 40 any time before or after processor 26 controls fluid delivery pump 32 to deliver a fluid dose to a patient through catheter 18 (step 54). For example, the baseline pressure can be measured upon implantation of therapy system 10 after a priming bolus has been delivered to fill catheter 18 with fluid. In another example, the baseline pressure can be measured just prior to fluid pump 32 delivering a fluid dose to patient 16 (step 54). In still another example, the baseline pressure can be measured before and after fluid pump 32 delivers the fluid dose (step 54) and processor 26 controls pressure sensor 40 to measure the pressure pulse (step 56).

In addition to measuring the baseline pressure (step 52), method 50 includes processor 26 controlling fluid delivery pump 32 to deliver a fluid dose to patient 16 through catheter 18 (step 54). As discussed with reference to therapy system 10 in FIGS. 1 and 2, catheter 18 may be connected to IMD 12, which includes fluid pump 32 configured to deliver a fluid therapeutic agent to patient 16 through the catheter. In examples according to this disclosure, a single stroke of fluid pump 32 may be configured to deliver a nominal fluid dose or pulse to patient 16 through catheter 18 with a relatively small volume and little or no therapeutic affect on the patient. For example, the volume of fluid agent delivered to patient 16 from a single stroke of one example pump mechanism could be as small as 1 micro liter. In this way, for purposes of determining the length of catheter 18, the fluid dose can be delivered to patient 16 through the catheter at virtually any time with little to no affect on the patient's therapy program or schedule.

The timing and frequency of the fluid dose that is delivered to the patient for purposes of examples according to this disclosure can vary depending on the intended application. For example, a nominal fluid dose could be delivered to the patient for purposes of initially determining the length of the catheter once shortly after the catheter is implanted within the patient, e.g., before activation of therapy programs. In any event, timing and frequency can be controlled by the control electronics within the IMD to which the implantable catheter is connected, e.g. processor 26 and memory 28 of IMD 12. For example, IMD 12 used in accordance with examples disclosed herein can include memory 28 that stores one or more algorithms that include instructions executed by processor 26 for periodically delivering nominal fluid doses to patient 16 in order to measure a pressure pulse within catheter 18 that is then used to estimate the length of catheter 18.

In another example, the algorithms can query when and how often the therapy program for IMD 12 delivers therapeutic doses to patient 16 to determine if additional nominal doses are necessary for purposes of estimating the length of catheter 18. In other words, IMD 12 can be configured to integrate the functions associated with examples of determining the length of catheter 18 with the execution of the therapy program of patient 16 by measuring the pressure within catheter 18 during delivery of a regularly scheduled therapeutic dose to the patient. The calculated length can then be used, i.e., plugged into, equations used to compute dosages for the therapy programs. In particular, each program may take into account catheter volume, as a function of catheter length, in computing dosages to be delivered to patient 16 in the ordinary course of therapy.

Method 50 also includes measuring a pressure pulse within the lumen during the delivery of the fluid dose (step 56). As described with reference to IMD 12 in FIGS. 1 and 2, pressure sensor 40 fluidly connected to implanted catheter 18 can measure the pressure within the lumen of catheter 18 at any time that fluid pump 32 is called upon to deliver a fluid dose to patient 16. Pressure sensor 40 can be any of a number of types of sensors that are capable of measuring the pressure within an implantable catheter including. Examples of pressure sensors include capacitive and inductive pressure sensors. The pressure measured by sensor 40 can be gauge or absolute pressure, but, in any event, will include a characteristic transient pressure pulse with a maximum pressure that is generated when the fluid dose is delivered as the pressure in catheter 18 increases slightly in reaction to the dose before settling back to a steady state, i.e., baseline pressure.

Figure 4:
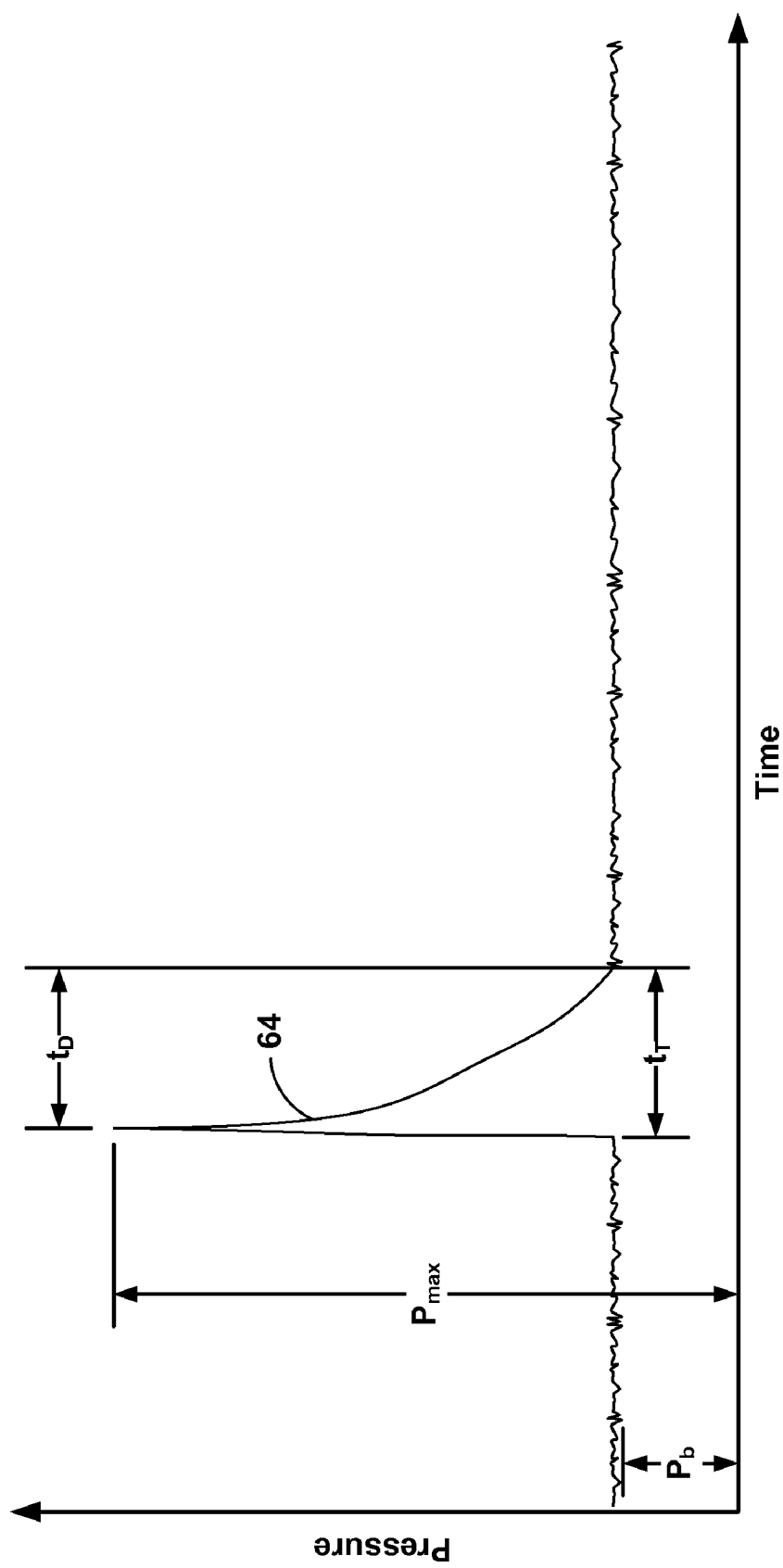
FIG. 4 is a plot of pressure versus time that illustrates the pressure within an implanted catheter during the delivery of a fluid dose to a patient.
Figure 5:
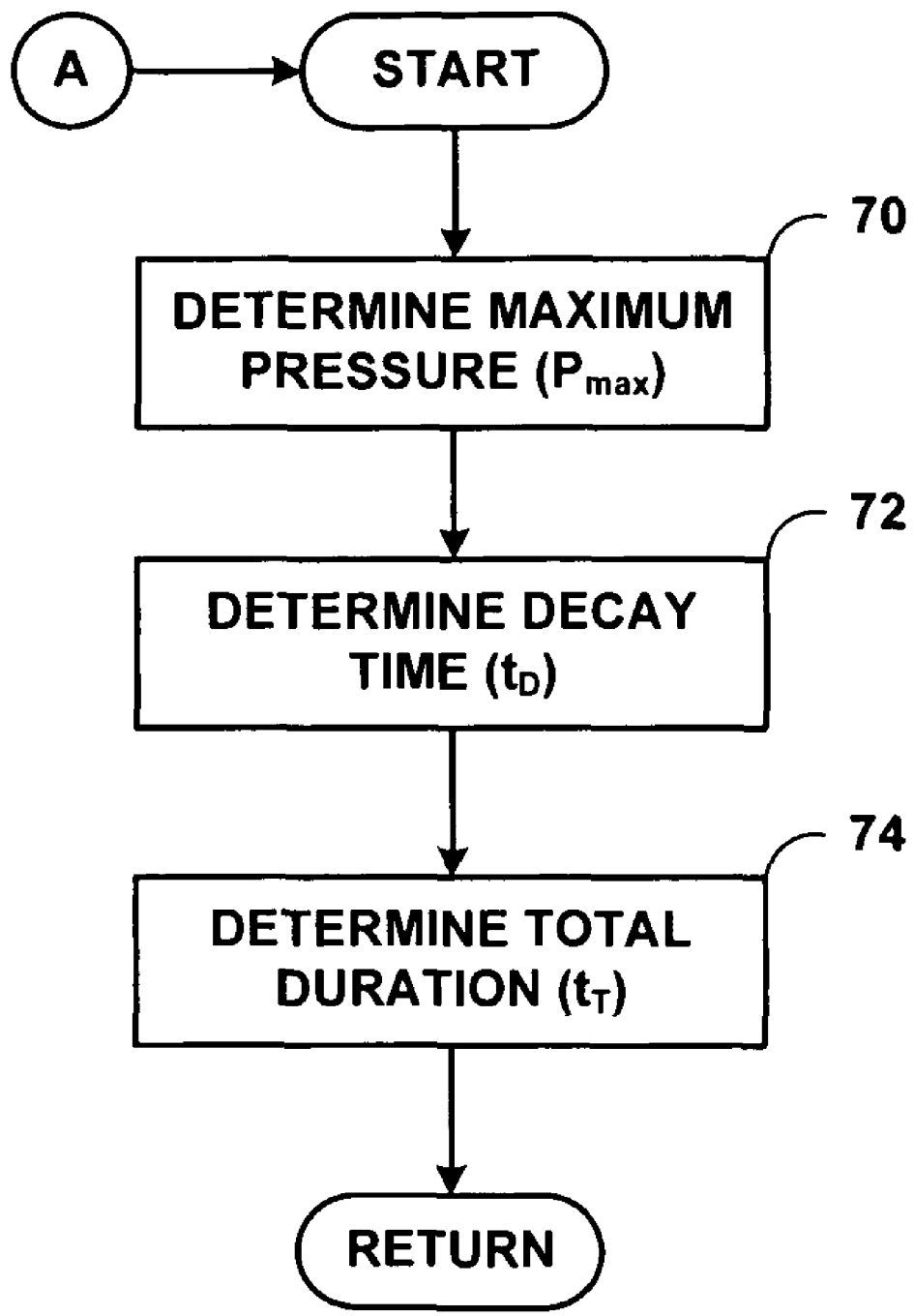
FIG. 5 is a flow chart illustrating examples by which a pressure pulse within an implantable catheter during the delivery of a fluid dose may be measured.

In order to better understand the response of an implantable catheter to fluid pressure inputs, a canine study was performed that, inter alia, measured pressure pulses within an implanted intrathecal catheter with varying lengths and/or defects. FIG. 4 illustrates a pressure pulse representative of results of this study. FIG. 4 is a plot of pressure versus time that illustrates the pressure within an implanted catheter during the delivery of a fluid dose to a patient. In FIG. 4, transient pressure pulse 64 is generated when the fluid dose is delivered through catheter 18 to patient 16. Pressure pulse 64 includes a maximum pressure, $P_{max}$ to which the pressure within catheter 18 climbs almost instantaneously from the baseline pressure, $P_B$ after the pump mechanism 32 of IMD 12 begins delivering the fluid dose to patient 16. Pressure pulse 64 also includes a total duration, $t_T$, and a decay time, $t_D$. The decay time $t_D$ is the time required for the pressure pulse within the lumen of catheter 18 to fall from the maximum pressure $P_{max}$ to the baseline pressure $P_B$. Because the pressure rises from the baseline pressure $P_B$ to the maximum pressure $P_{max}$ almost instantaneously, in many cases the total duration $t_T$ of pressure pulse 64 may be almost equal to the decay time $t_D$.

As illustrated in FIG. 4, the pressure pulse within the lumen that is measured in methods according to this disclosure has several distinct characteristics. Therefore, in the examples disclosed herein, measuring the pressure pulse (step 56) can include, e.g., processor 26 of IMD 12 further analyzing the pressure measurement data received from pressure sensor 40 to determine one or more of the maximum pressure (step 70), the decay time (step 72), and the total duration (step 74) of the pressure pulse as illustrated in the flow chart of FIG. 5.

It was discovered from the canine study that the pressure pulse waveform, such as the pressure pulse 64 shown in FIG. 4, for a normally functioning catheter with a length of approximately 80 centimeters generated a maximum pressure of about 10.66 KPa. The catheter used in the study was model number 8709 manufactured by Medtronic, Inc. of Minneapolis, Minn. The rise from the baseline pressure was nearly instantaneous relative to a 250 hertz sampling rate that was used to measure pressure within the catheter. The form of the decay from the maximum pressure back to the baseline was exponential (as illustrated in FIG. 4) with a decay constant on the order of 0.038 seconds and total decay time approximately equal to 0.100 seconds.

Referring again to FIG. 3, in addition to measuring a pressure pulse within the lumen during the delivery of the fluid dose (step 56), method 50 includes calculating an estimated length of catheter 18, e.g., via processor 26, based on the measured pressure pulse (step 58). The pressure change within the lumen of catheter 18 caused by delivering a fluid dose therethrough, i.e., the pressure pulse, is a function of, at least in part, the length of the catheter. Therefore, the length of a properly functioning implanted catheter 18 can be estimated with reasonable accuracy based on the magnitude and/or characteristics of the pressure pulse measured within the lumen during the delivery of the fluid dose to patient 16 (step 56).

Figure 6:
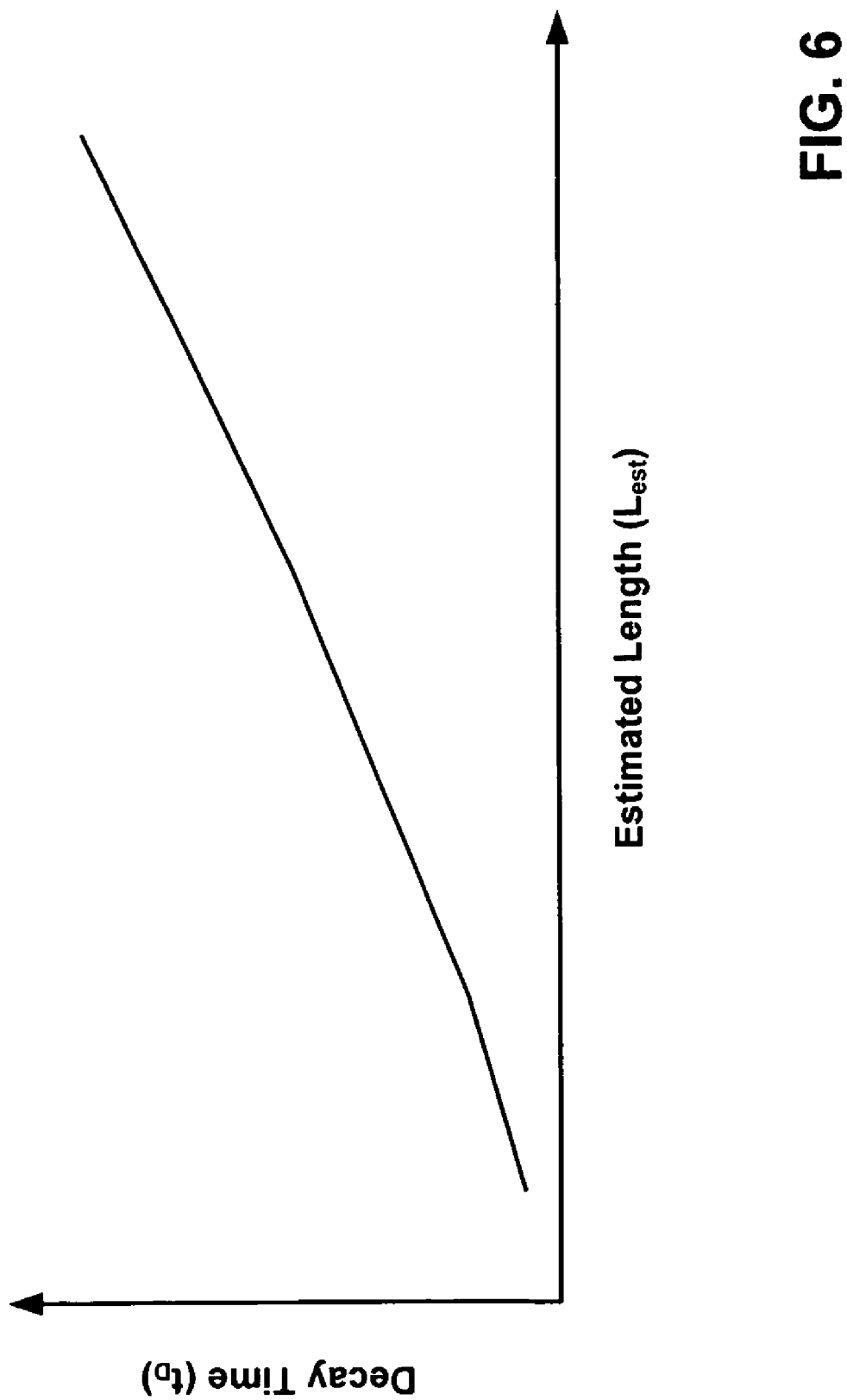
FIG. 6 is a plot of catheter length versus pressure pulse decay time that illustrates the relationship of catheter length to pressure within the delivery lumen of a normally functioning catheter.

For example, calculating the estimated length of catheter 18 based on the measured pressure pulse (step 58) can include processor 26 calculating the estimated length based on the decay time ($t_D$) of the pressure pulse. As explained above with reference to FIG. 4, the decay time of the pressure pulse can, in many cases, be virtually equal to the total duration of the pressure pulse ($t_T$) because the pressure rises almost instantaneously from the baseline ($P_B$) to a maximum pressure ($P_{max}$). FIG. 6 is a plot of catheter length versus pressure pulse decay time that illustrates the relationship of length to pressure within the delivery lumen of a normally functioning catheter. The curve shown in FIG. 6 is representative of experimental data generated by measuring pressure pulse decay times for a catheter as the length of the catheter was varied. In general, the length of the implanted catheter is directly proportional to the decay time of the pressure pulse generated during delivery of a fluid dose through the catheter. As illustrated in FIG. 6, the length of the catheter increases linearly as the decay time of the pressure pulse increases, and decreases linearly as the decay time decreases.

In the canine study discussed above with reference to FIG. 4, an implanted intrathecal catheter was continuously cut to shorten the catheter from full length to near-zero length (e.g. cut at or near the exit port from the IMD to which the catheter was connected). As the location of the cut in the catheter moved closer to the exit port of the IMD, i.e. as the catheter length decreased, the decay time of the pressure pulse decreased from 0.100 seconds down to zero seconds in a linear manner. As a percentage of the full length of the implanted catheter, the decay time of the pressure pulse decreased from 0.100 seconds at full length to 0.060 seconds at 80% of full length, 0.040 seconds at 50% of full length, and 0.020 seconds at 25% of full length. Using an experimental relationship such as that illustrated in FIG. 6 and described with reference to the canine study, the estimated length of catheter 18 can be calculated by processor 26 based on the decay time of the pressure pulse generated within the lumen of catheter 18 when fluid pump 32 delivers the fluid dose to patient 16.

In general, calculating the estimated length of catheter 18 may depend not only on properties or characteristics of the measured pressure pulse, but also on the particular fluidic resistance characteristics of the catheter including, e.g., fluidic resistance per unit length and volumetric compliance per unit length. In some examples, catheter 18 may be of a known type with known characteristics that may be stored, e.g., in memory 28 of IMD 12 (or in another location, e.g. memory on external programmer 20). In such examples, processor 26 of IMD 12 may retrieve key characteristics (e.g. fluidic resistance per unit length and volumetric compliance per unit length) of catheter 18 from a look-up table stored in memory 28 or memory in programmer 20. Processor 26 may then account for the catheter characteristics retrieved from memory 28 in the calculation of the estimated length of catheter 18. In other examples, catheter 18 may be of a known type, but with unknown characteristics. The type of catheter 18 may, in such examples, be stored in memory 28 of IMD 12. In another example, neither the type nor any of the characteristics of catheter 18 are known and/or stored. In examples where either or both of the type or characteristics of catheter 18 are unknown and/or unrecorded, catheter characteristics relevant to length calculations may be assumed to provide a range boundary to the estimated length calculation. In any of the examples incorporating catheter characteristics, IMD 12 may communicate with external programmer 20 to provide an alert or other notification to a user, e.g. patient and/or clinician, that prompts the user to, e.g., provide or augment any missing or incorrect catheter information or notifies the user whenever any assumptions are applied to the estimated length calculations.

Using the fluidic resistance characteristics of catheter 18 and the above described characteristics of the measured pressure pulse, the length of catheter 18 may be estimated analytically instead of by referencing experimental data as described above with reference to FIG. 6. In such cases, the overall pump catheter system including, e.g. fluid pump 32 and catheter 18 may be approximated by an electrical analog that represents fluidic restriction (e.g. represented as resistance) and compliance (e.g. represented as capacitance), and pressure (e.g. represented as power) of the various components of and at various locations in the system model. In some examples, the dominant characteristics of the electrical analog model are the fluidic resistance and compliance of catheter 18. The input signal to the system may be a relatively rapid, e.g. less than approximately 0.005 seconds, pressure pulse that is assumed to be a unit-impulse response to a fluid dose delivered through catheter 18. Within the overall system model, catheter 18 may itself behave as a distributed restriction and compliance model having an equivalent model that may be represented by a single or lumped restriction and compliance value including, e.g., the total fluidic resistance of the catheter.

The length of catheter 18 can be estimated by determining the total fluidic resistance of the catheter, because the total fluidic resistance is equal to the length of the catheter multiplied by a fluidic resistance per unit length constant for the catheter. In general, the fluidic resistance per unit length constant of catheter 18 is dependent on the size, shape, and material properties of the catheter lumen. In one example system model, the instantaneous flow rate of fluid within catheter 18 is equal to the differential pressure across the length of the catheter divided by the total fluidic resistance of the catheter. The volume of fluid dispensed into catheter 18 is equal to the integral of flow rate over time and may be assumed to be a constant including, e.g. a nominal dose equal to approximately 1 micro liter. Therefore, the dispensed volume is equal to a constant, which is equal to the integral of the differential pressure across the length of catheter 18 divided by the total fluidic resistance of the catheter over time. Compliance in the overall system and in catheter 18 is the physical property that creates the exponential decay of the measured pressure pulse illustrated and described above with reference to FIG. 4. The integral of the measured exponential pressure pulse over time is proportional to the volume of fluid dispensed through catheter 18. In particular, the integral of the measured pressure pulse is equal to the total fluidic resistance of catheter 18 multiplied by the dispensed volume. Therefore, the total fluidic resistance of catheter 18 is equal to the integral of the measured pressure pulse divided by the volume of dispensed fluid, i.e. is equal to a constant including, e.g. 1 micro liter. The total fluidic resistance of catheter 18 can therefore be calculated from the measured pressure pulse and the known volume of the fluid dose delivered to patient 12. The length of catheter 18 is equal to total fluidic resistance divided by the fluidic resistance per unit length constant for the catheter.

Figure 7:
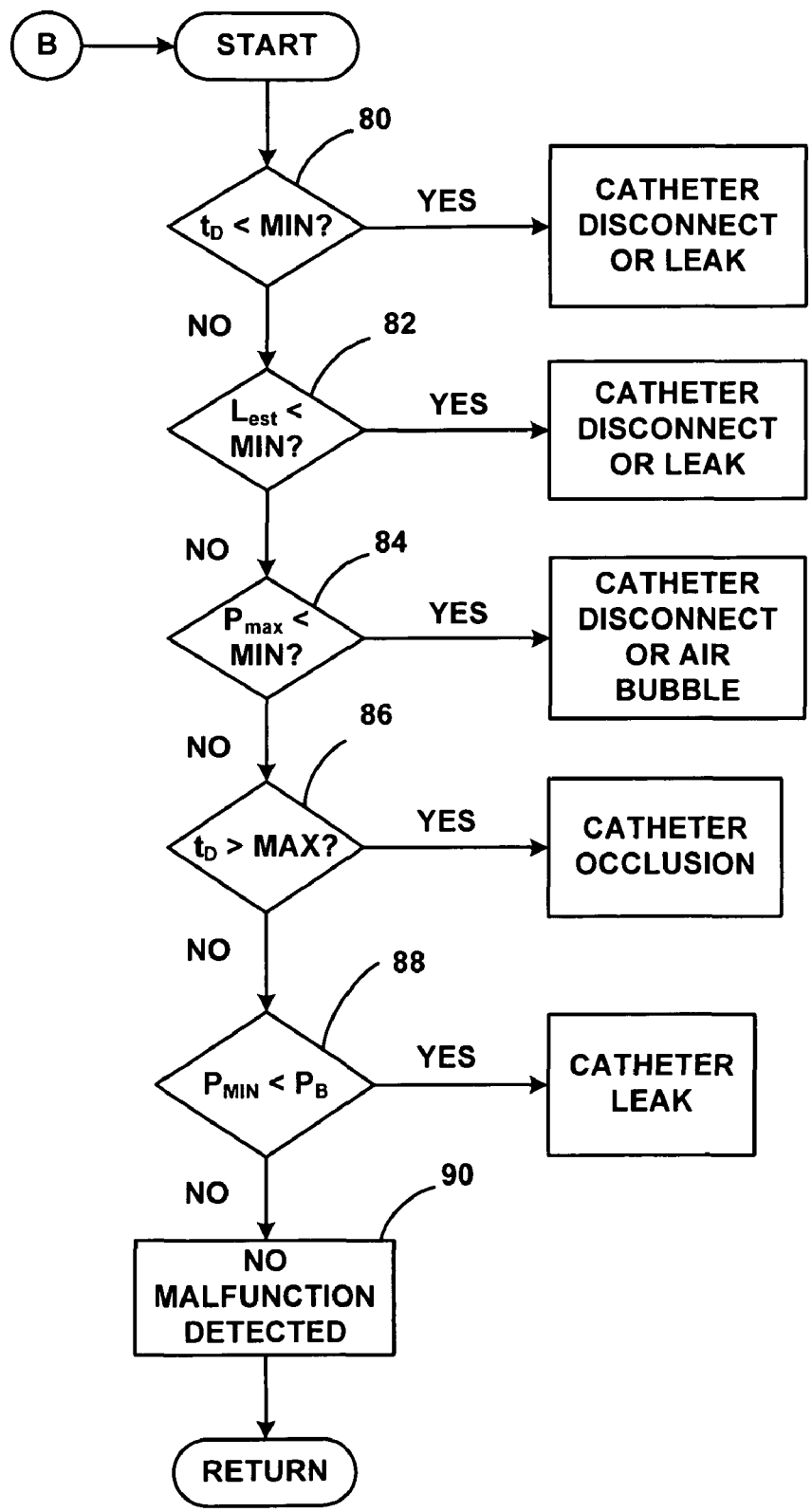
FIG. 7 is a flowchart illustrating examples for determining if an estimated length calculated according to disclosed examples is representative of the actual length of a catheter.

Method 50 also may include analyzing the estimated length to determine if it is representative of an actual length of catheter 18 (step 60). For example, processor 26 of IMD 12 can analyze the estimated length calculation to determine if it is representative of the actual length of catheter 18, or if it has been affected by, e.g., one or more defects in or malfunctions of catheter 18. FIG. 7 is a flowchart illustrating a number of examples by which processor 26 of IMD 12 may determine if the estimated length calculated in examples disclosed herein is representative of the actual length of catheter 18 (step 60). In one example shown in FIG. 7, processor 26 can compare the decay time ($t_D$) of the pressure pulse generated within the lumen of catheter 18 to a minimum threshold value to determine if the catheter is disconnected from IMD 12 or contains a cut or leak proximate IMD 12 (step 80). In a similar manner, processor 26 can also compare the estimated length ($L_{est}$) to a minimum threshold value to determine if catheter 18 is disconnected or contains a cut or leak (step 82). If catheter 18 is cut proximate to or is disconnected from IMD 12, the estimated length calculated by processor 26 based on the measured pressure pulse will be relatively small because the decay time of the pressure pulse, which is proportional to the length of catheter 18, will have a smaller magnitude than a normally functioning catheter. Therefore, processor 26 of IMD 12 can compare the calculated estimated length of catheter 18 and/or the decay time of the pressure pulse to a minimum value to determine if catheter 18 is disconnected or has a leak and therefore is not exhibiting a length estimate that is representative of the actual length of catheter 18.

The magnitude of the minimum length threshold to which the estimated length of catheter 18 is compared may vary depending on, e.g. the type of therapy being delivered and the implantation location of IMD 12 and the target drug delivery site within patient 16. For example, an average catheter length for intrathecal fluid drug delivery may be approximately equal to 80 centimeters. The average or typical length for catheter 18 may be used to set a threshold minimum that represents catheter lengths that are outside of range above and below the typical length.

In another example, processor 26 of IMD 12 can compare a maximum pressure within the lumen of catheter 18 to a minimum threshold value to determine if catheter 18 is disconnected from IMD 12 or contains an air bubble (step 84). As explained with reference to FIG. 4, during the delivery of a fluid dose to patient 16 a characteristic pressure pulse will exhibit a maximum pressure, $P_{max}$, to which the pressure within catheter 18 climbs from a baseline pressure, $P_B$, after the fluid pump 32 of IMD 12 begins delivering the fluid dose to patient 16. In the case catheter 18 is disconnected from IMD 12 or contains an air bubble, the maximum pressure of the pressure pulse may have an unusually low value.

Generally speaking, the decay time of the measured pressure pulse is directly proportional to the maximum pressure, making the magnitude of the pressure generated within catheter 18 during the delivery of a fluid dose directly proportional to the length. Therefore, lower maximum pressures will generally indicate shorter decay times and shorter lengths of catheter 18. A minimum pressure threshold may be set that represents pressures indicating lengths of catheter 18 that are unusually low for the particular therapeutic application of IMD 12. As with the minimum length threshold described above, the average or typical length for catheter 18 may be used to set a threshold minimum pressure that represents pressure values that will yield catheter lengths that are outside of range above and below the typical length.

In addition to referencing average or typical catheter lengths, the magnitude of the minimum pressure threshold may be set based on experimental data for different types of catheters of varying lengths. For example, in the above referenced canine study it was determined that the maximum pressure for the a cut or disconnected catheter having near-zero length falls off from around 10.66 KPa for a full length normally functioning catheter to a value around 4 KPa. Additionally, the study showed that air bubbles trapped within the pressure circuit, e.g. within catheter 18 dampen the magnitude of the maximum pressure of the pressure pulse by a factor of 10. Once a minimum pressure threshold value is set, processor 26 of IMD 12 can compare the maximum pressure of the pressure pulse measured by pressure sensor 40 during delivery of the fluid dose to patient 16 to the minimum to determine if catheter 18 may be disconnected from IMD 12 or contains an air bubble and therefore is not exhibiting a length estimate that is representative of the actual length of catheter 18.

In still other examples, processor 26 of IMD 12 can compare the decay time of the pressure pulse generated within the lumen of catheter 18 to a maximum threshold value to determine if catheter 18 includes an occlusion (step 86). In some examples in which catheter 18 includes an occlusion along the length thereof, the pressure pulse generated within catheter 18 during delivery of a fluid dose to patient 16 may reach a maximum pressure, but may not decay to the baseline pressure before a subsequent fluid dose delivery. In such examples, a second dose delivered to patient 16 by fluid pump 32 may then raise the pressure in the lumen of catheter 18 to a second maximum followed by a drop to another elevated pressure that is again above the baseline pressure. This transient pressure pulse behavior may be caused by the fluid being trapped within catheter 18 by the blockage. Because the pressure within catheter 18 does not drop to the baseline pressure, the decay time cannot be measured based on the pressure data provided by pressure sensor 40. In such examples, processor 26 of IMD 12 can compare the decay time of the pressure pulse measured by pressure sensor 40 during delivery of the fluid dose to patient 16 to a maximum to determine if catheter 18 is occluded and therefore is not exhibiting a length estimate that is representative of the actual length of catheter 18.

Figure 8:
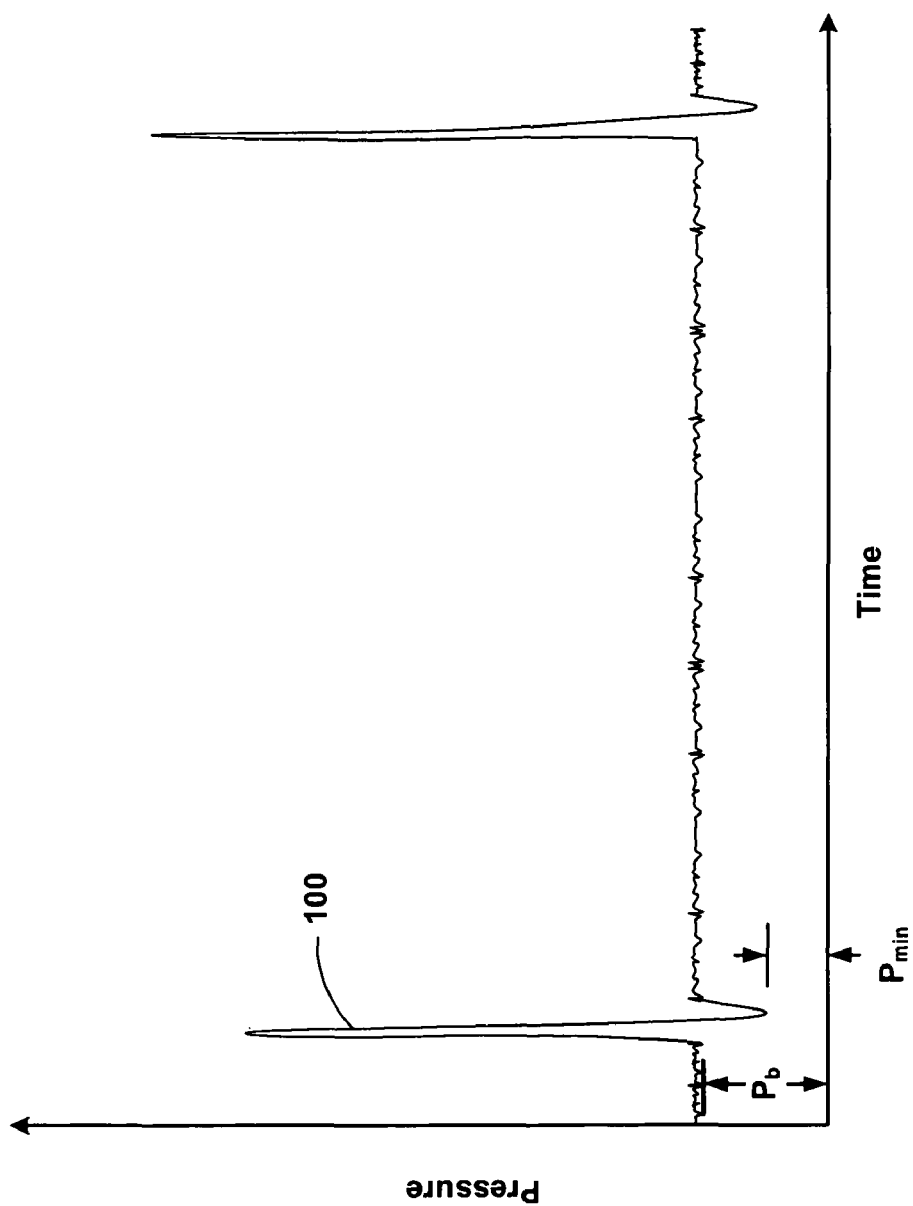
FIG. 8 is a plot of pressure versus time that illustrates the pressure within a cut or leaking catheter during a delivery of a fluid dose to a patient.

Still referring to FIG. 7, in another example, processor 26 of IMD 12 can compare a minimum pressure within catheter 18 during delivery of a fluid dose to patient 16 to the baseline pressure to determine if catheter 18 has a cut or leak (step 88). In some cases where catheter 18 includes a cut or leak very close to IMD 12, the pressure pulse generated during delivery of the fluid dose may exhibit a characteristic negative minimum pressure below the baseline pressure as illustrated in FIG. 8. FIG. 8 is a plot of pressure versus time that illustrates the pressure within an implanted catheter during the delivery of a fluid dose to a patient. The pressure pulse shown in FIG. 8 is representative of a catheter that has a cut close to a proximal end thereof connected to an IMD. In FIG. 8, transient pressure pulse 100 is generated when the fluid dose is delivered through catheter 18 to patient 16. Pressure pulse 100 includes a maximum pressure to which the pressure within catheter 18 climbs from the baseline pressure, $P_B$, after the pump mechanism 32 of IMD 12 begins delivering the fluid dose to patient 16.

In contrast to the example that compares the maximum pressure to a minimum threshold described above with reference to step 84 of FIG. 7, the maximum pressure of pressure pulse 100 reaches a level typically associated with a properly functioning catheter 18. However, pressure pulse 100 decays to a minimum pressure, $P_{min}$, that is less than the baseline pressure. The negative minimum pressure illustrated by pressure pulse 100 in FIG. 8 may occur because a catheter cut close to or at the proximal connection to the IMD behaves like an undamped system in which the pressure drops more rapidly from the maximum pressure and therefore overshoots the baseline pressure by a non-trivial amount. For example, in the canine study previously referenced, the pressure pulse for a cut catheter rose and decayed quickly, and then dropped below the baseline pressure by approximately 1.33 KPa. In examples including a pressure pulse with such a characteristic negative minimum pressure, processor 26 of IMD 12 can compare a minimum pressure of the pressure pulse measured by pressure sensor 40 to a baseline pressure to determine if catheter 18 is cut and therefore is not exhibiting a length estimate that is representative of the actual length of catheter 18.

In the event that processor 26 of IMD 12 determines that the analysis performed in all of steps 80-88 illustrated in FIG. 7 produces negative results, processor 26 may conclude that catheter 18 contains no malfunctions (step 90) and that the estimated length is representative of the actual length of the catheter. If positive results are produced, processor 26 may detect a catheter malfunction and generate an appropriate alert to the patient and/or clinician. The alert may be a tactile, audible or visible alert presented via the IMD 12 or external programmer 20.

Once the estimated length of catheter 18 has been analyzed and deemed satisfactory by, e.g., the process illustrated in FIG. 7, IMD 12 may store the estimated length in memory 28 and/or present the length to a user. For example, an implanting physician may use therapy system 10 including catheter length estimation means according to this disclosure to confirm the proper implantation of catheter 18 within patient 16. In such examples, processor 26 of IMD 12 may implement a method according to this disclosure to calculate an estimated length of catheter 18 after the physician has implanted therapy system 10 within patient 16. IMD 12 may store the estimated length of catheter 18 in memory 28 from which it may be accessed and/or transmitted to other devices by processor 26.

For example, processor 26 may transmit the estimated length calculation to external programmer 20 to be displayed via a user interface thereon. In this way, the implanting physician, or any other authorized user may access the estimated length calculated by IMD 12. In some cases, the estimated length calculation may be used by processor 26 to compute or recompute dosages for therapy programs. In other cases, if the estimated length calculation is generally consistent with a previously estimated length calculation, e.g., by the clinician or otherwise, processor 26 takes no action and does not compute or recompute dosages. Hence, processor 26 may generate an alert in the event a malfunction is detected, or generate an alert in the event the estimated catheter length is inconsistent with a previous catheter length determination.

Figure 9:
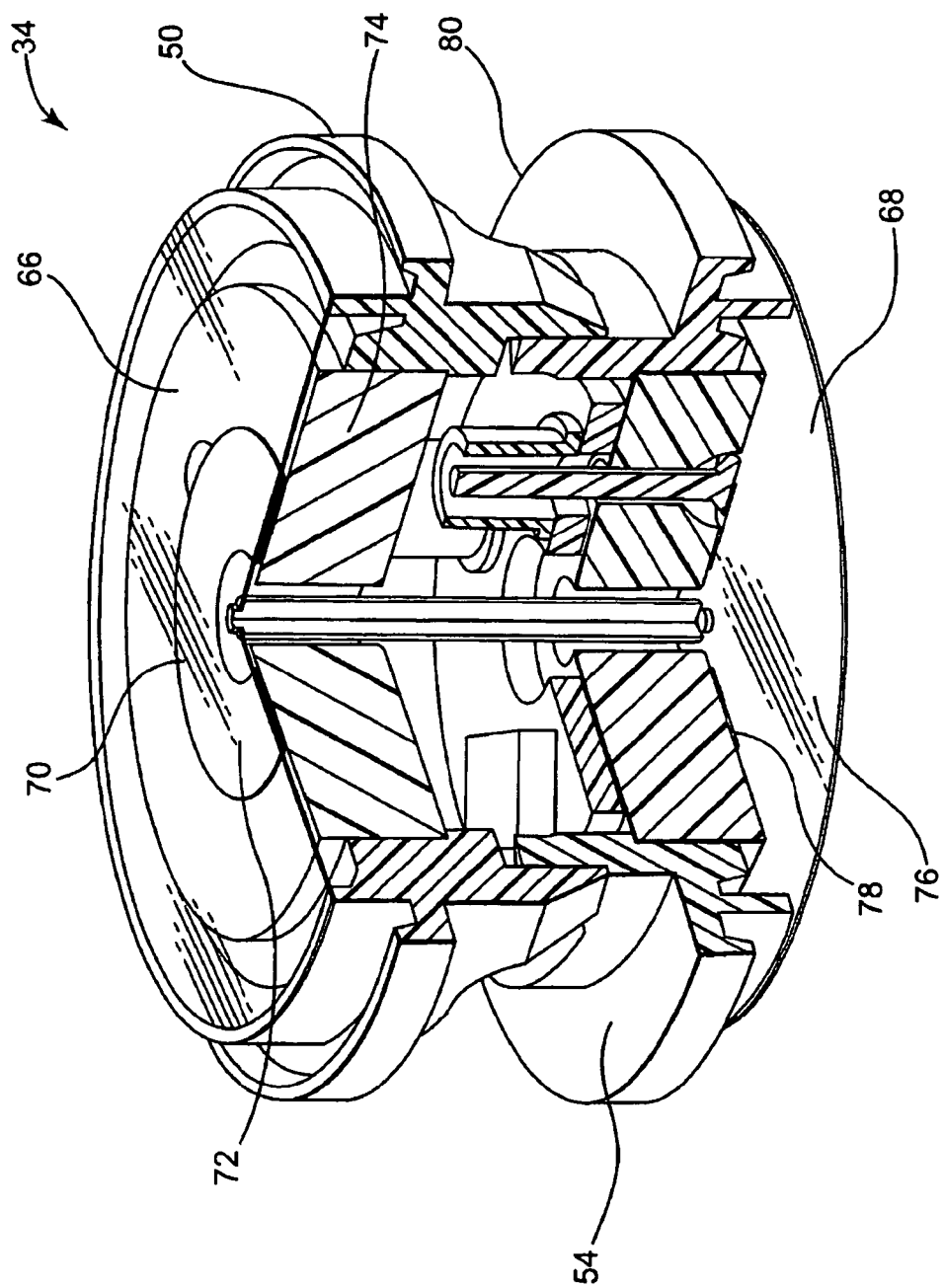
FIG. 9 is a partial cross-sectional view of an example capacitive pressure sensor.
Figure 10:
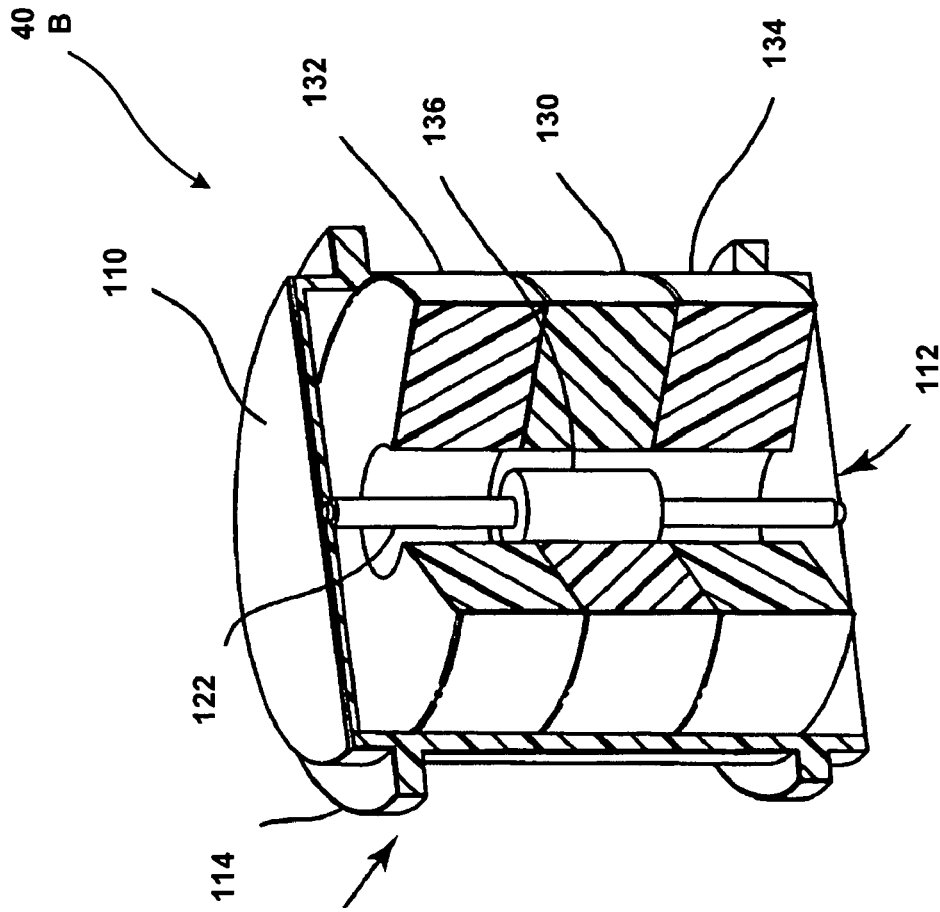
FIG. 10 is a partial cross-sectional view of an example inductive pressure sensor.

FIGS. 9 and 10 show examples of pressure sensor appropriate for use with methods and systems according to this disclosure. FIG. 9 is a partial cross-sectional view of an example pressure sensor 40A including upper diaphragm 110, lower diaphragm 112, sensor casing 114, conductive material 116, complementary conductive material 118, stationary insulator 120, coupler 122 and capacitive sensor 124. In FIG. 9, sensor 40A is a capacitive flow sensor utilizing two diaphragms 110 and 112. Upper diaphragm 110 is mounted to sensor casing 114. Upper diaphragm 110 may be made from or coated, at least partially, with a conductive material 116. Complementary conductive material 118 may be coated on stationary insulator 120, which may, in some examples, be a sapphire insulator. In one example, a 0.002 inch gap is created between conductive materials 116 and 118. Using air as an insulator, conductive materials 116 and 118 form a capacitor. As upper diaphragm 110 moves in response to pressure changes, the capacitance created by conductive materials 116 and 118 also changes.

A similar arrangement exists on the opposite end of sensor casing 114 with lower diaphragm 112. Conductive materials 116 and 118 are coated on lower diaphragm 112 and sapphire insulator 120, respectively, forming another capacitor. Coupler 122 is positioned for relative movement with, preferably against, both upper diaphragm 110 and lower diaphragm 112. Capacitive sensors 124 are sensitive to changes in capacitances from movement of each of upper and lower diaphragms 112 and may provide the pressure measurements from within catheter 18 used in examples according to this disclosure.

The dual diaphragm and dual capacitor arrangement described with reference to FIG. 9 actually multiplies the amount of change in capacitance with a given amount of movement in diaphragms 110 and 112. Since the pressure changes are small, the movement of diaphragms 110 and 112 are small. The capacitance change is additive resulting in twice the performance. In one example, coupler 126 contacts diaphragms 110 and 112 in the center of the diaphragms in order to obtain the maximum movement of the diaphragms. Coupler 126 should not significantly inhibit the movement of diaphragms 110 and 112.

FIG. 10 illustrates example pressure sensor 40B which operates on a change in inductance and includes upper diaphragm 110, lower diaphragm 112, coupler 122, center primary coil 130, upper secondary coil 132, lower secondary coil 134, and magnetic element 136. In FIG. 10, sensor 40B again has two diaphragms 110 and 112 with coupler 122 mounted for movement therebetween. A center primary coil 130 is arranged is configured to be excited with an alternating current. Upper and lower secondary coils, 132 and 134 respectively, are mounted above and below primary coil 130, respectively. Magnetic element 136 is mounted for movement with coupler 122. As magnetic element 136 moves up and/or down in response to changes in pressure, the inductance induced in secondary coils 132 and 134 varies. An inductance sensor (not shown) can detect the change in these inductances and provide an output indicative of a change in pressure. Again, this arrangement doubles the effectiveness of movement in diaphragms 110 and 112 by additively combining the changes in inductance of each individual secondary coil 132, 134.

Examples presented in this disclosure may augment or replace the need for manually entering the catheter length in implantable fluid delivery systems, thereby promoting accuracy in the calculation of dosing durations including, e.g. the duration of a bridge or priming bolus. The techniques described herein include therapy systems with one or more pressure sensors configured to measure pressure somewhere within an IMD fluid pathway (e.g. a catheter attached thereto, and/or internal tubes within the IMD) while a dose of the therapeutic agent is delivered to the patient. The IMD in such therapy systems, and/or another device may be configured to calculate an estimated length of the catheter based on the measured pressure.

Calculating the length of the catheter without relying on human intervention (e.g. implanting physician measuring and recording length) can assist in and improve properly delivering, e.g., priming and bridging boluses, or any other doses in which catheter length is critical to proper and safe delivery of the therapeutic agent to the patient. In some cases, the automatically determined catheter length may be used in computing doses, or used as a cross-verification check to ensure the reasonable accuracy of catheter length determinations made by a clinician or other caregiver. The disclosed methods and systems can be important when a patient changes clinics or is out of the area in which his or her clinic is located and needs to have a pump refilled with a new drug, i.e. needs a bridging bolus. If the catheter type and length is not available, this method would allow a reasonable estimate of the dead space to be calculated for the switch over from one drug to another.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described herein. These and other examples are within the scope of the following claims.

The invention claimed is:

1. An implantable fluid delivery system comprising:
    a fluid delivery pump;
    a catheter connected to the fluid delivery pump;
    a pressure sensor arranged to measure a pressure in a lumen of the catheter; and
    a processor that:
        controls the fluid delivery pump to deliver an amount of fluid through the catheter;
        controls the pressure sensor to measure a pressure within the lumen of the catheter during the delivery of the fluid through the catheter; and
        calculates an estimated length of the catheter from a connection to the fluid delivery pump to a distal end of the catheter based on the measured pressure.

2. The system of claim 1 further comprising an implantable medical device that includes the fluid delivery pump and the processor.

3. The system of claim 1 further comprising an external programmer that includes the processor.

4. The system of claim 1, wherein the processor determines a maximum pressure within the lumen, and calculates the estimated length based on the maximum pressure.

5. The system of claim 4, wherein the processor determines a decay time required for the pressure within the lumen to fall from the maximum pressure to a baseline pressure, and calculates the estimated length based on the decay time.

6. The system of claim 5, wherein the pressure falls exponentially from the maximum pressure.

7. The system of claim 1, wherein the processor determines a total duration that the pressure is above a baseline pressure, and calculates the estimated length based on the total duration.

8. The system of claim 1, wherein the processor calculates the estimated length of the catheter based on a decay time required for a pressure within the lumen to fall from a maximum pressure to a baseline pressure during the delivery of the fluid.

9. The system of claim 1, wherein the processor controls the pressure sensor to measure a baseline pressure within the lumen while no fluid is being delivered through the catheter.

10. The system of claim 9, wherein the processor controls the pressure sensor to measure the baseline pressure prior to controlling the fluid delivery pump to deliver the fluid through the catheter.

11. The system of claim 1, wherein the processor analyzes the estimated length to determine if the estimated length is representative of an actual length of the catheter.

12. The system of claim 11, wherein the processor analyzes the measured pressure to identify one or more characteristics indicative of one or more catheter malfunctions.

13. The system of claim 12, wherein the processor analyzes the measured pressure to determine if a maximum pressure of the measured pressure is below a minimum pressure threshold value.

14. The system of claim 12, wherein the processor determines if a decay time required for a pressure within the lumen to fall from a maximum pressure to a baseline pressure is below a minimum threshold value.

15. The system of claim 12, wherein the processor determines if a decay time required for a pressure within the lumen to fall from a maximum pressure to a baseline pressure is above a maximum threshold value.

16. The system of claim 12, wherein the processor determines if a pressure within the lumen falls below a baseline pressure after decaying from a maximum pressure.

17. The system of claim 1, wherein the processor accounts for one or more characteristics of the catheter in the calculation of the estimated length.

18. The system of claim 17 further comprising a memory, and wherein the processor retrieves one or more of the catheter characteristics from a look-up table stored in the memory.

19. The system of claim 17 further comprising an external programmer, and wherein the processor receives one or more of the catheter characteristics from the external programmer.

20. The system of claim 17, wherein the characteristics of the catheter comprise one or more of fluidic resistance per unit length and volumetric compliance per unit length.

21. A computer-readable medium comprising instructions for causing a programmable processor in an implantable fluid delivery system to:
    control a fluid delivery pump to deliver an amount of fluid through an implantable catheter connected to the fluid delivery pump;
    control a pressure sensor to measure a pressure within a lumen of the catheter during the delivery of the fluid through the catheter; and
    calculate an estimated length of the catheter from a connection to the fluid delivery pump to a distal end of the catheter based on the measured pressure.

22. A device comprising:
    means for delivering an amount of fluid through an implantable catheter;
    means for measuring a pressure within a lumen of the catheter during the delivery of the fluid through the catheter; and
    means for calculating an estimated length of the catheter from a first end of the catheter connected to the means for delivering to a second end of the catheter based on the measured pressure.

* * * * *